(12) United States Patent
Babakhani et al.

(10) Patent No.: US 10,408,774 B2
(45) Date of Patent: Sep. 10, 2019

(54) EPR SYSTEMS FOR FLOW ASSURANCE AND LOGGING

(71) Applicant: WILLIAM MARSH RICE UNIVERSITY, Houston, TX (US)

(72) Inventors: Aydin Babakhani, Houston, TX (US); Xuebei Yang, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 290 days.

(21) Appl. No.: 15/022,307

(22) PCT Filed: Sep. 25, 2014

(86) PCT No.: PCT/US2014/057402
§ 371 (c)(1),
(2) Date: Mar. 16, 2016

(87) PCT Pub. No.: WO2015/048249
PCT Pub. Date: Apr. 2, 2015

(65) Prior Publication Data
US 2016/0223478 A1    Aug. 4, 2016

Related U.S. Application Data

(60) Provisional application No. 61/882,296, filed on Sep. 25, 2013.

(51) Int. Cl.
*G01V 3/32* (2006.01)
*G01N 24/10* (2006.01)
(Continued)

(52) U.S. Cl.
CPC .............. *G01N 24/10* (2013.01); *E21B 49/08* (2013.01); *G01R 33/3607* (2013.01);
(Continued)

(58) Field of Classification Search
CPC ... E21B 2049/085; E21B 49/08; G01N 24/10; G01R 33/3607; G01R 33/3621;
(Continued)

(56) References Cited

U.S. PATENT DOCUMENTS 3,348,136 A    10/1967  Nelson et al.
5,233,303 A *   8/1993  Bales ............... G01R 33/60
                                               324/316

(Continued)

OTHER PUBLICATIONS

L. J. Bond, et. al., "Evaluation of Non-Nuclear Techniques for Well Logging: Technology Evaluation", U.S. Department of Energy, PNNL-19867, Nov. 2010.
(Continued)

*Primary Examiner* — Tung X Nguyen
*Assistant Examiner* — Robert P Alejnikov, Jr.
(74) *Attorney, Agent, or Firm* — Winstead PC

(57) ABSTRACT

An Electron Paramagnetic resonance (EPR) system and method allows the measurement paramagnetic characteristics of materials in real-time, such as heavy oil, hydrocarbons, asphaltenes, heptane, vanadium, resins, drilling fluid, mud, wax deposits or the like. The EPR systems and methods discussed herein are low cost, small and light weight, making them usable in flow-assurance or logging applications. The EPR sensor is capable of measuring paramagnetic properties of materials from a distance of several inches. In some embodiments, a window will be used to separate the EPR sensor from the materials in a pipeline or wellbore. Since the sensor does need to be in direct contact with the materials, it can operate at a lower temperature or pressure. In other embodiments, the EPR sensor may be placed in the materials.

22 Claims, 12 Drawing Sheets

(51) Int. Cl.
  *G01R 33/36*  (2006.01)
  *G01R 33/60*  (2006.01)
  *G01V 3/26*  (2006.01)
  *E21B 49/08*  (2006.01)
  *G01R 33/381*  (2006.01)
  *G01R 33/44*  (2006.01)

(52) U.S. Cl.
  CPC ......... *G01R 33/3621* (2013.01); *G01R 33/60* (2013.01); *G01V 3/26* (2013.01); *G01V 3/32* (2013.01); *E21B 2049/085* (2013.01); *G01R 33/381* (2013.01); *G01R 33/448* (2013.01)

(58) Field of Classification Search
  CPC .... G01R 33/381; G01R 33/448; G01R 33/60; G01V 3/26; G01V 3/32
  USPC ................. 324/300–322; 600/407–435; 382/128–131
  See application file for complete search history.

(56) References Cited

U.S. PATENT DOCUMENTS

| | | | | |
|---|---|---|---|---|
| 6,169,396 | B1* | 1/2001 | Yokotani | G01D 5/147 324/207.12 |
| 2001/0028247 | A1* | 10/2001 | King | G01R 33/60 324/312 |
| 2007/0152789 | A1* | 7/2007 | Watanabe | G01R 33/3815 335/216 |
| 2007/0216406 | A1* | 9/2007 | Witcraft | G01R 33/09 324/252 |
| 2009/0115416 | A1* | 5/2009 | White | G01N 24/08 324/316 |
| 2009/0121712 | A1* | 5/2009 | Han | G01R 33/282 324/307 |
| 2009/0146755 | A1* | 6/2009 | Liu | H01F 17/0013 333/181 |
| 2012/0197117 | A1* | 8/2012 | Picot | A61B 5/0059 600/438 |
| 2013/0093424 | A1* | 4/2013 | Blank | G01R 33/60 324/316 |
| 2014/0091802 | A1 | 4/2014 | Yang et al. | |
| 2014/0097842 | A1 | 4/2014 | Yang et al. | |

OTHER PUBLICATIONS

A. Babakhani, D. B. Rutledge, and A. Hajimiri, "Transmitter Architectures Based on Near-Field Direct Antenna Modulation (NFDAM)," in IEEE J. Solid-State Circuits, vol. 43, No. 12, pp. 2674-2692, Dec. 2008.

A. Babakhani, X. Guan, A. Komijani, A. Natarajan, and A. Hajimiri, "A 77 GHz Phased Array Transceiver with On-Chip Dipole Antennas: Receiver and Antennas," in IEEE J. Solid-State Circuits, vol. 41, No. 12, pp. 2795-2806, Dec. 2006.

A. Natarajan, A. Komijani, X. Guan, A. Babakhani, and A. Hajimiri, "A 77 GHz Phased Array Transceiver with On-Chip Dipole Antennas: Transmitter and Local LO-Path Phase Shifting," in IEEE J. Solid-State Circuits, vol. 41, No. 12, pp. 2807-2819, Dec. 2006.

S. Jeon, Y. Wang, H. Wang, F. Bohn, A. Natarajan, A. Babakhani, and A. Hajimiri, "A Scalable 6-to-18 GHz Concurrent Dual-Band Quad-Beam Phased-Array Receiver in CMOS," in IEEE J. Solid-State Circuits, pp. 2660-2673, Dec. 2008.

J. Buckwalter, A. Babakhani, A. Komijani, and A. Hajimiri, "An Integrated Subharmonic Coupled-Oscillator Scheme for a 60-GHz Phased-Array Transmitter," in IEEE Transactions on Microwave Theory and Techniques, vol. 54, No. 12, pp. 4271-4280, Dec. 2006.

A. Hassibi, A. Babakhani, and A. Hajimiri, "A Spectral-Scanning Nuclear Magnetic Resonance Imaging (MRI) Integrated Transceiver," in IEEE J. Solid-State Circuits, vol. 44, No. 6, pp. 1805-1813, Jun. 2009.

T. Chen, et. al., "On the High-Temperature (to 300 C.) Characteristics of SiGe HBTs," in IEEE Transactions on Electron Devices, vol. 51, No. 11, pp. 1825-1832, Nov. 2004.

X. Yang, P. Seifi, and A. Babakhani, "A Single-Chip Dual-Mode CW/Pulse Electron Paramagnetic Resonance Spectrometer in 0.13 μm SiGe BiCMOS," in IEEE MTT-S Int. Microwave Symposium, Jun. 2013.

C. Chen, P. Seifi, and A. Babakhani, "A Silicon-Based, Fully Integrated Pulse Electron Paramagnetic Resonance System for mm-Wave Spectroscopy," in IEEE MTT-S Int. Microwave Symposium, Jun. 2013.

G. K. Wong, et. al., "An electron spin resonance probe method for the understanding of petroleum asphaltene macrostructure", Journal of Petroleum Science and Engineering, vol. 28, pp. 55-64, 2000.

C. L. B. Guedes, et. al., "Photochemical weathering study of Brazilian petroleum by EPR spectroscopy", Journal of Marine Chemistry, vol. 84, pp. 105-112, 2003.

C. Poole, "Electron Spin Resonance: A Comprehensive Treatise on Experimental Techniques," John Wiley & Sons, p. 443, 1982.

Eurasian Patent Office; Official Notification; dated Nov. 24, 2017; Application No. 201690632; William Marsh Rice University.

* cited by examiner

EPR SYSTEMS FOR FLOW ASSURANCE AND LOGGING

CROSS-REFERENCE TO RELATED APPLICATIONS

This application claims priority to U.S. Provisional Patent Application No. 61/882,296, filed on Sep. 25, 2013. The entirety of the aforementioned application is incorporated herein by reference.

FIELD OF THE INVENTION

This invention relates to methods and systems utilizing electron paramagnetic resonance (EPR) to detect the characteristics of materials. More particularly, to utilizing EPR systems or methods to detect the characteristics of materials in wells, pipelines or formations, such as for flow assurance or logging.

BACKGROUND OF INVENTION

Electron paramagnetic resonance (EPR) phenomenon is based on interaction of electron spins with electromagnetic fields in the presence of an external DC magnetic field. EPR data provides valuable information about electronic structures and spin interactions in paramagnetic materials. EPR has found wide-ranging applications in various science and engineering technology areas, such as studying chemicals involving free radicals or transition metal ions. EPR spectrometers comprise components that are expensive, heavy, and large in weight and physical dimensions. Because of the high cost ($500 k), large size (1 $m^3$), and large weight (100 kG) of EPR spectrometers, EPR spectrometers are unsuitable for use in wells or pipelines.

As discussed herein, the integration of EPR circuitry in a single chip makes EPR less costly and more portable. A dual mode EPR sensor or spectrometer discussed herein may be manufactured using a silicon process, and may be capable of performing both continuous wave (CW) and time-domain (pulse) measurements. The EPR systems and methods discussed herein may be utilized to gather data regarding conditions of a well, pipeline or formation. Further, EPR systems and methods may be utilized to provide flow assurance and logging.

SUMMARY OF THE INVENTION

In one embodiment, components of an EPR spectrometer may comprise a transceiver, a magnetic field generator with adjustable magnetic field, and a loop-gap resonator. In some embodiments, the EPR spectrometer may be positioned adjacent to a window of a pipeline. Further, the magnetic field generator may produce a magnetic field, more particularly a DC magnetic field. The magnetic field generator may comprise magnets, coils, or a combination thereof that are positioned outside or inside of the pipeline to generate a magnetic field. A transceiver of the EPR spectrometer may provide a pulsed or continuous signal to a resonator to generate a pulsed or continuous RF magnetic field approximately normal to a DC magnetic field of the magnets or coils. A receiver of the EPR spectrometer may monitor the reflected signal to detect changes in reflected signal. The changes in the reflected signal may be analyzed to determine the materials present, material concentrations, and their location in the pipeline. This may allow for realtime detection of asphaltenes, heptane, wax, other deposits, and combinations thereof.

In another embodiment, the EPR spectrometer may be positioned adjacent to a window in a downhole or logging tool that is suitable for placement in a wellbore. Magnets, coils, or a combination thereof may be positioned outside or inside of the logging tool to generate a magnetic field. A transceiver of the EPR spectrometer may provide a pulsed or continuous signal to a resonator to generate a pulsed or continuous RF magnetic field approximately normal to a DC magnetic field of the magnets or coils. A receiver of the EPR spectrometer may monitor the reflected signal to detect changes in reflected signal. The changes in the reflected signal may be analyzed to determine the materials present, material concentrations, and their location in the wellbore. This may allow for realtime detection of hydrocarbons, heavy oil, makeup of the formation, asphaltenes, and combinations thereof.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
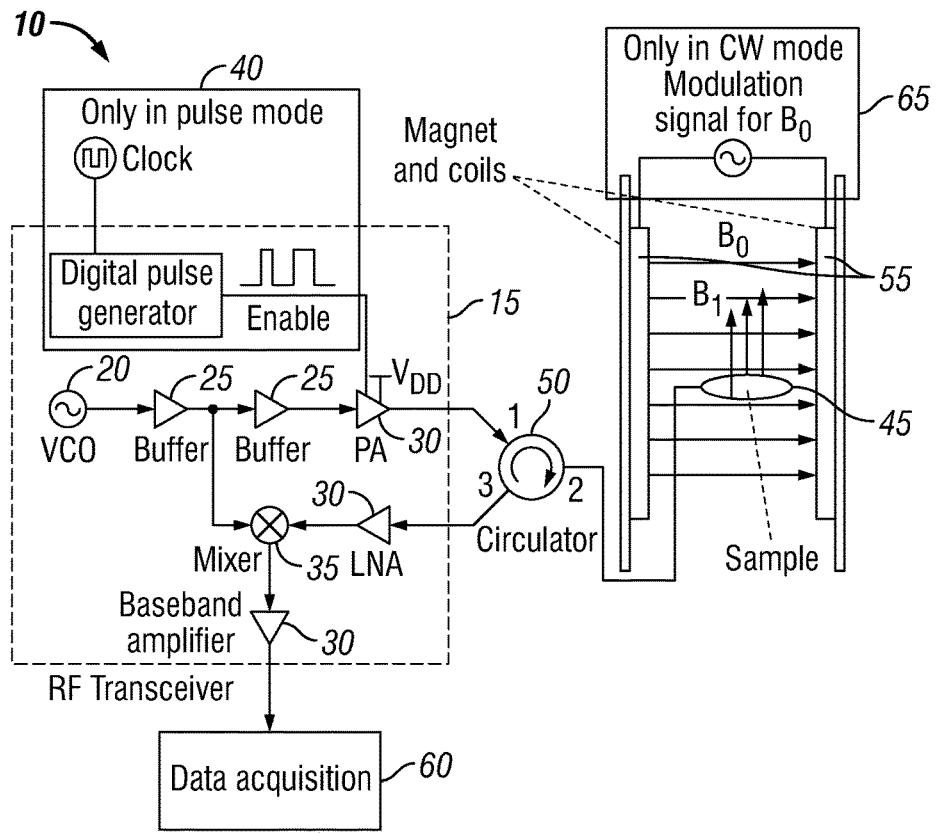
FIG. 1 is an illustrative embodiment of a block diagram of an electron paramagnetic resonance (EPR) sensor.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

An Electron Paramagnetic resonance (EPR) system and method to measure paramagnetic characteristics of materials in real-time, such as, but not limited to, heavy oil, hydrocarbons, asphaltenes, vanadium, resins, drilling fluid, mud, wax deposits or the like. The EPR systems and methods discussed herein are low cost, small and light weight, making them usable in flow-assurance or logging applications. The EPR sensor is capable of measuring paramagnetic properties of materials from a distance of several inches. In some embodiments, a window will be used to separate the EPR sensor from the materials while allowing a RF signal to easily penetrate the window to monitor the materials. As a nonlimiting embodiment, a window may be a portion of tubular of a pipeline or a portion of a downhole tool that provides a material with high transparency to electromagnetic waves. Since the sensor does need to be in direct contact with the materials, it can operate at a lower temperature or pressure. In other embodiments, the EPR sensor may be placed in the materials and operate in high temperature or pressure.

In some embodiments, the EPR sensor may provide detection of asphaltenes concentration and prediction of asphaltenes precipitation. In some embodiments, the sensor may be suitable for detecting asphaltenes concentrations of 10,000 ppm or less from a distance of 3 inches or less. In some embodiments, the sensor may be suitable for detecting asphaltenes concentrations of 5,000 ppm or less from a distance of 2 inches or less. In some embodiments, the sensor may be suitable for detecting asphaltene concentrations of 500 ppm or less from a distance of 1 inch or less. In some embodiments, EPR sensor may measure wax deposition in pipelines or wells. In some embodiments, the EPR sensor may be utilized as an imaging system to capture 3-D EPR images of the cross section of a pipeline or well. In some embodiments, the EPR sensor may be utilized as an imaging system to capture 2-D EPR images of the formation. In one embodiment, the EPR sensor is a sensor that operates at 1 GHz or higher. In other embodiments, the EPR sensor may operate at higher frequencies, such as 100 MHz or higher, 10 GHz (X-band) or higher, equal to or between 30 GHz to 300 GHz (mm-wave band). Although conventional EPR sensors exist, due to the large size (e.g. in the range of $m^3$) of these spectrometers they cannot be used in down-hole applications. In a down-hole environment, the size of the sensor, including the transceiver, magnetic field generator, and resonator should be smaller than several inches. For example, in some embodiments, the size of the sensor may be equal to or less than 100 $cm^3$. In other embodiments, the size of the sensor may be equal to or less than 50 $cm^3$. In other embodiments, the size of the sensor may be equal to or less than 5 $cm^3$. In some embodiments, the weight of the sensor may be 50 kg or less. In some embodiments, the weight of the sensor may be 10 kg or less. In some embodiments, the weight of the sensor may be 5 kg or less. In order to keep the size of the sensor small, the EPR sensor may be able to operate with a small permanent magnet (rare-earth magnet).

An EPR sensor or spectrometer for detecting or measuring electron paramagnetic or electron spin resonance is discussed herein. Components of the EPR spectrometer may comprise a single-chip transceiver, a magnetic field generator with adjustable magnetic field, and a planar microstrip parallel loop-gap resonator. FIG. 1 is an illustrative embodiment of a block diagram of an EPR sensor 10, where an on-chip transceiver 15 is shown in the dashed section. A transceiver may allow the EPR sensor to send and receive RF signals. The transceiver may include a voltage controlled oscillator (VCO) 20, one or more buffers 25, one or more amplifiers 30 (e.g. power, baseband, low noise, variable gain, or the like), and mixer 35. In some embodiments, the transceiver may also include a clock and pulse generator 40 that are suitable for providing a pulse EPR mode of operation. The RF signal provided by the transceiver 15 may be provided to a resonator 45, such as a loop-gap resonator. In some embodiments, a circulator 50 may be coupled to the transceiver 15 and resonator 45. A magnetic field generator 55 may produce a magnetic field, and data acquisition 60 may be utilized to store desired data. In some embodiments, a modulator 65 may be desirable for magnetic field generated by the magnetic field generator 55.

The magnetic field generator provides a DC magnetic field utilizing magnets, coils, or the like. A sample and resonator are placed inside magnets and/or coils that generate a DC magnetic field, $B_0$, also known as Zeeman field. As a nonlimiting example, the magnets or coils may be positioned inside or outside of a tubular of a pipeline near the resonator so that fluid flowing through the pipeline can be monitored. Presence of this external field introduces an energy difference $\Delta E$ between the two spin states of an unpaired electron: parallel and anti-parallel to $B_0$, with $\Delta E$ being proportional to $B_0$. In its resonance frequency, the resonator produces a RF magnetic field $B_1$. At the RF frequency where hf equals $\Delta E$ (Larmor frequency), where h is the Planck constant, spin transitions between the two up and down spin states occur, resulting in absorption of RF energy in the sample. In a reflection type resonator, this results in a change in the level of reflected power from the resonator. The EPR sensor may be capable of performing both continuous wave (CW) and time-domain (pulsed) measurements.

Figure 2A:
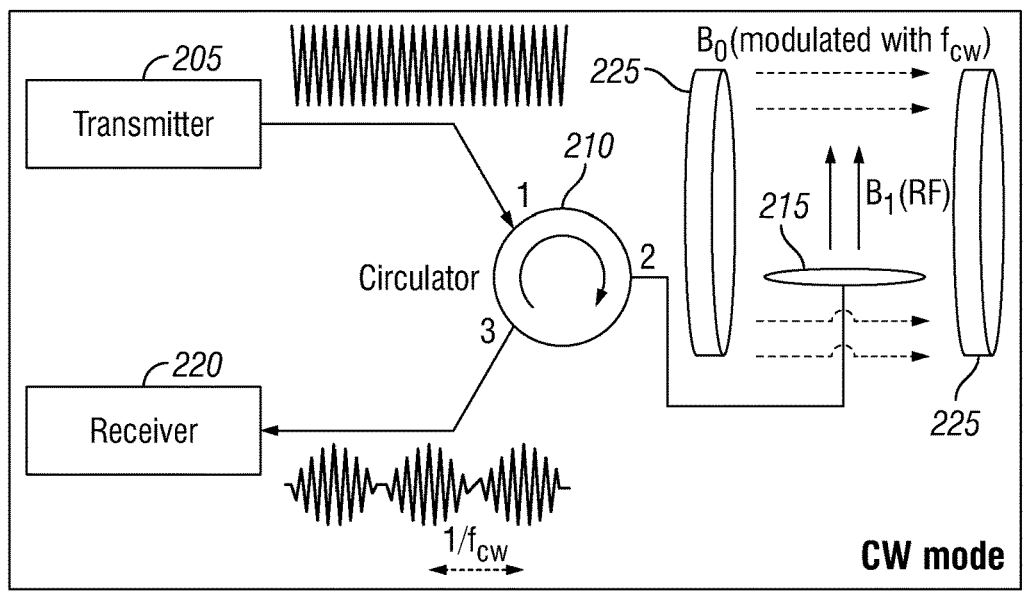
FIGS. 2A-2B is an illustrative embodiment of continuous wave (CW) and time-domain (pulsed) EPR modes.
Figure 2B:
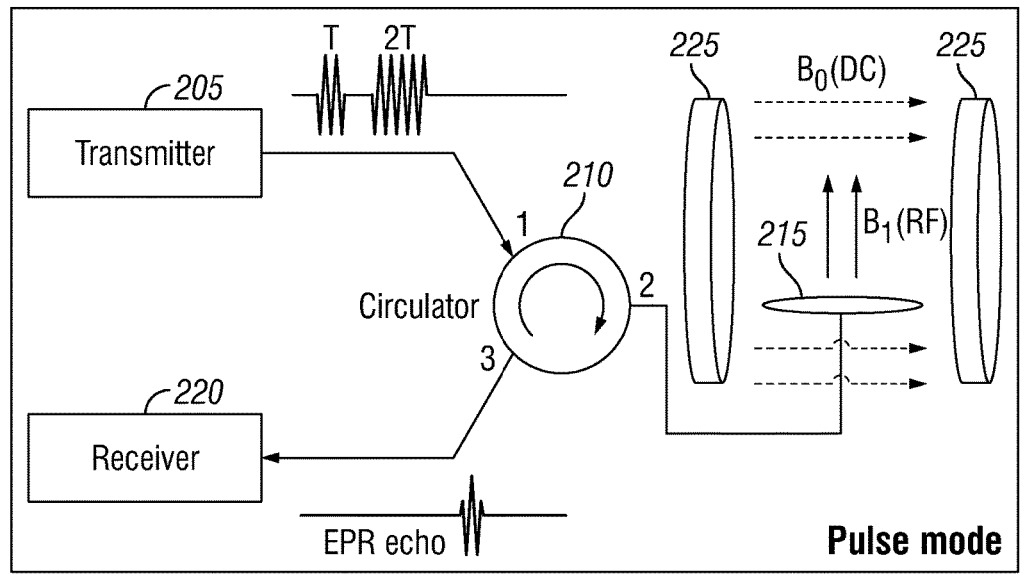

Operation principles of CW and pulse EPR modes are illustrated in FIGS. 2A-2B. Further discussion of EPR principles and techniques can be found in J. A. Weil and J. R. Bolton, *Electron Paramagnetic Resonance: Elementary Theory and Practical Applications*, John Wiley & Sons, 2007; Gilbert et al., *Electron Paramagnetic Resonance*, Volume 20, The Royal Society of Chemistry, Cambridge UK 2007; and A. Schweiger and G. Jeschke, *Principles of Pulse Electron Paramagnetic Resonance*, Oxford University Press, 2001, which are all incorporated by reference herein.

A brief description of the two modes of EPR is as following: in both modes, the sample is placed at the center of an RF resonator inside a DC magnetic field, $B_0$. In CW-EPR, a continuous RF signal is sent by the transmitter 205 to the resonator 215 through a circulator 210 and the change in reflected power is monitored by a receiver 220. A magnetic field generator 225 may provide a DC magnetic field ($B_0$) that is normal to an RF magnetic field ($B_1$) produced by the resonator 215. The RF power absorbed by the sample can be calculated as a function of the DC magnetic field or as a function of the frequency of the RF magnetic field and plotted. The absorbed power may vary with the $B_0$ field or frequency of $B_1$ and this absorption line shape reveals paramagnetic properties of the sample. For example, the absorption line shape may be analyzed to determine the presence of materials, such as asphaltenes, wax or the like. In some embodiments, a modulator may be provided to reduce the effect of low-frequency noise (1/f), e.g. $B_0$ is modulated and the reflected power is measured at the modulation frequency.

In pulse-EPR, the transmitter 205 sends a sequence of RF pulses through circulator 210 to the resonator 215 used to generate an RF magnetic field, $B_1$, normal to the DC field, $B_0$, produced by magnetic field generator 225 which results in flipping of the spins of the unpaired electrons. The external magnetic field causes precession of the perpendicular or transverse component of the magnetization vector around the $B_0$ axis. Furthermore, an interaction of electron spins with each other and with nearby nuclei spins results in relaxation of perpendicular (transverse) and parallel (longitudinal) components of the magnetization with respect to $B_0$. At the end, the magnetization vector (spin) is aligned with $B_0$. The precession of the transverse component generates a time-domain signal detected by the resonator (free induction decay) that can be provided to receiver 220. The time-domain signal from spin relaxation may be recorded. More complicated echo signals can be generated in studying spin interaction mechanisms. The subsequent time-domain signal from spin relaxation is then recorded. Wideband spectral information of the EPR samples is reproduced using Fourier transform techniques applied to the EPR transient response. The time-domain or echo signals may be monitored to detect the presence of materials, such as asphaltenes, heptane, wax or the like. As a nonlimiting example, the time-domain EPR echo signal may be recorded after the sample is excited by two or more pulses. The longitudinal relaxation due to spin-lattice interaction (T1) and/or transverse relaxation due to spin-spin interaction (T2) may be measured to determine paramagnetic properties of the fluid that allow the EPR sensor to detect the presence of materials, material concentrations, or the like.

In flow assurance, an EPR system may be utilized in realtime detection of asphaltenes, wax or other deposits and in prediction of asphaltenes precipitation. In some embodiments, an EPR sensor and a resonator are placed inside the pipeline or well. In some embodiments, an EPR sensor is placed outside the pipeline or well, but the resonator is placed inside. In some embodiments, an EPR sensor and a resonator are placed outside the pipeline or well adjacent to a window in a pipeline or well. A magnetic field generator (e.g. magnets and/or coils) may be placed inside or outside of the pipeline/well. A power supply may be provided by the drilling or logging tools to power the EPR sensor and magnetic field generator. In sub-sea flow-assurance, the power supply maybe provided by wired connections. In other embodiments, a power supply may be provided using any other suitable methods for supplying power downhole.

In a CW-EPR mode, a continuous signal may be provided by a transceiver to a resonator to generate a continuous RF magnetic field $B_1$ approximately normal to a DC magnetic field $B_0$ of the magnets or coils. If coils are utilized, the coils are energized to create the DC magnetic field $B_0$. Changes in reflected power as a function of DC magnetic field are received by the transceiver of the EPR sensor and may be monitored to determine the RF power absorbed by fluid in the pipeline or well. For example, the EPR sensor may be coupled to a data acquisition module that gathers RF power absorption data, plots RF power absorption v. the DC magnetic field to provide a RF power absorption plot in realtime, and monitors a line shape of the power absorption data. In another embodiment, the RF power absorption plot provided in realtime may be RF power absorption v. frequency of the signal $B_1$. The height, width, as well as the zero-crossing point of the line shape of the RF power absorption plot may reveal the paramagnetic properties of the fluid, thereby allowing the presence or concentration of materials, such as asphaltenes, wax or the like to be determined. As asphaltenes molecules aggregate or precipitate, their magnetic field impacts the EPR response of the adjacent molecules. As asphaltene aggregation increases, the width of the line shape becomes larger. Thus, the wave width can be utilized to determine the amount of asphaltene that has aggregated or precipitated. The wave height increases with increasing asphaltene concentration. Thus, the wave height can be utilized to determine a concentration of asphaltenes. The data acquisition module may compare the gathered power absorption data to known data corresponding to certain concentrations of materials. Gathered power absorption data is match up to known data within a desired accuracy, and the concentrations of materials can be determined by the particular concentration associated with the known data accordingly. As a nonlimiting example, a table of several different concentrations of asphaltene that are each associated with different known data points is scanned to locate the known data that matches the power absorption data detected, thereby allowing the concentration of asphaltene to be determined.

In a CW-EPR mode, the continuous excitation signal provided by the transmitter may couple to the input of the receiver. This coupled signal, known as the TX leakage, may saturate the receiver and distort the EPR signal. In some embodiments, an active cancelation block may be used to reduce or cancel the TX leakage. The active cancelation block senses the output of the TX, generates a precise cancelation signal with the same amplitude but inverted phase in comparison to the TX leakage, and combines the cancelation signal with the receiver input. The TX leakage will thus be removed after the combination due to the inverted phase and identical amplitude of the cancelation signal. To achieve effective cancelation, this combined signal may be monitored in real-time and a feedback mechanism may be used to adjust the cancelation signal.

In a pulse EPR mode, the arrangement of the EPR sensor and magnets and/or coils is as discussed above. However, the transceiver provides a pulsed signal to the resonator. The precession of the transverse component of a magnetization vector (see above discussion of pulse EPR) generates a time domain signal detected by the resonator, and provided to the transceiver of the EPR sensor. In some embodiments, more complicated echo signals can be generated to measure the $T_1$, and $T_2$ relaxation times of the spins. The time domain signal may be analyzed to determine the type, phase, and concentration of asphaltenes or wax in the fluid. A line shape of the time domain signal may reveal the paramagnetic properties of the fluid, thereby allowing the presence or concentration of materials, such as asphaltenes, wax or the like, to be determined. The data acquisition module may compare the time domain signal to known data representing corresponding to certain concentrations of materials. When the time domain signal matches known data within a desired accuracy, the concentrations of materials can be determined by the concentrations associated with the known data.

In logging, the EPR sensor can be used to determine the type of hydrocarbons, heavy oil, makeup of the formation and asphaltenes. This logging tool can operate with both water- and oil-based muds. Imaging may be conducted as discussed above for CW-EPR and pulse EPR modes. The EPR logging data can be combined with the NMR and resistivity logs to provide additional information about the reservoirs. In some embodiments, an EPR sensor may be placed at a window in a logging tool. Magnets and/or coils may be placed inside or outside of the logging tool. A power supply may be provided by the logging tools.

Experimental Example

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Figure 3:
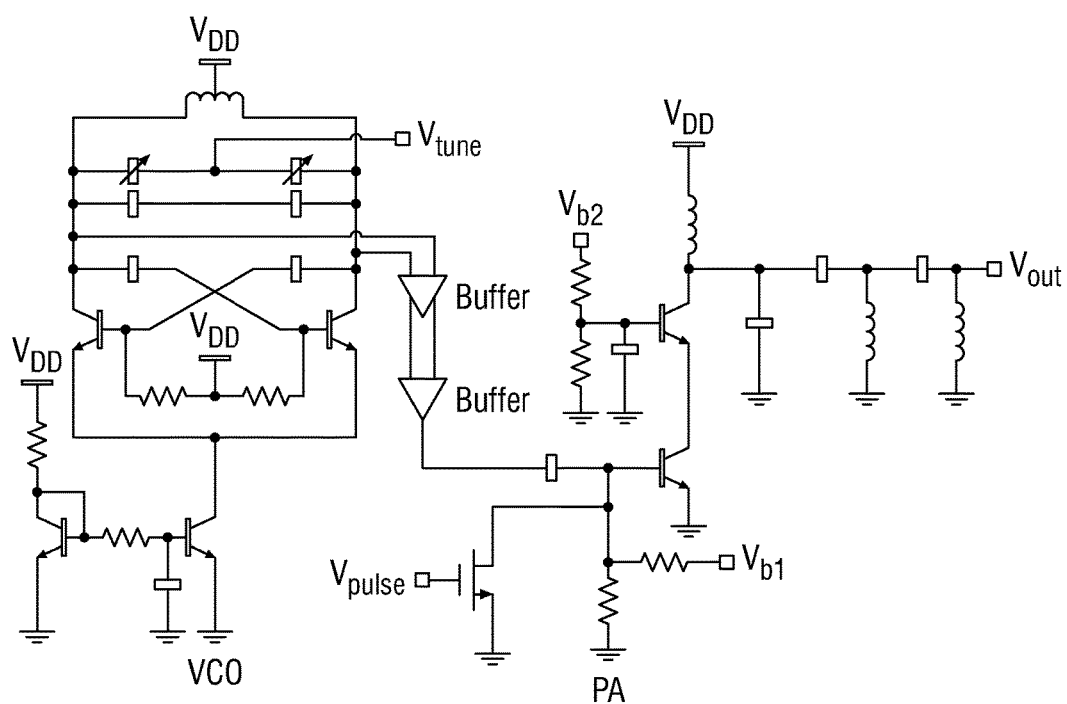
FIG. 3 is an illustrative embodiment of a circuit topology for a voltage controlled oscillator (VCO) and power amplifier (PA)
Figure 4:
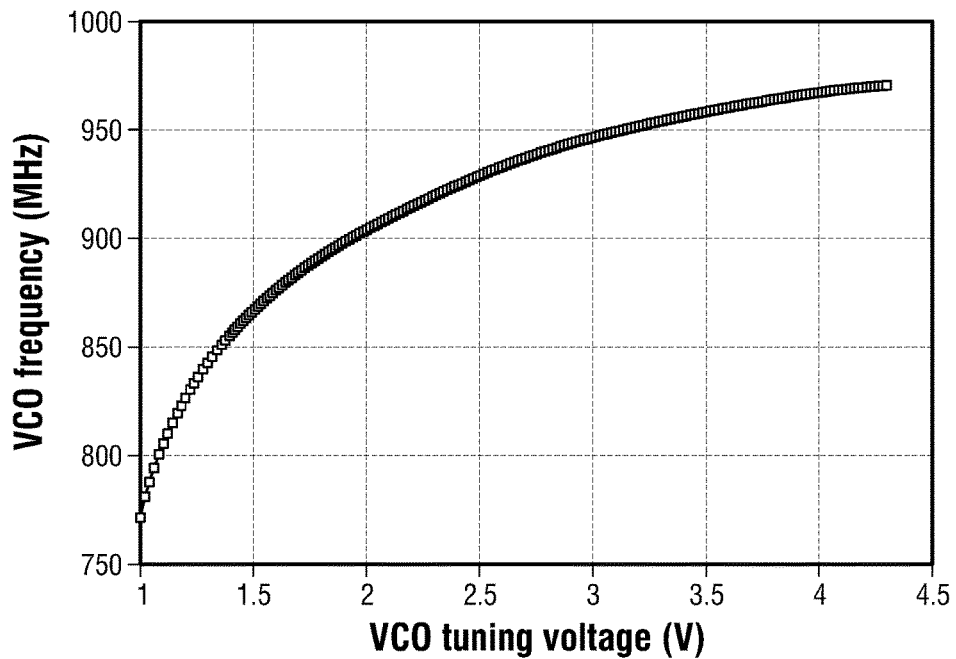
FIG. 4 is an illustration of a relationship between the VCO frequency and the tuning voltage.

The integrated EPR spectrometer was tested using ~50 mg of 2,2-Diphenyl-1-Picrylhydrazyl (DPPH) powder at room temperature. The Zeeman field is set to around 340 G (0.034 T), corresponding to 950 MHz absorption frequency. This frequency of operation is chosen as a compromise: lower frequencies would result in lower SNR, yet at higher frequencies generating magnetic fields for portable systems would be problematic. The RF signal is generated using an onchip voltage controlled oscillator (VCO). The VCO, shown in FIG. 3 with power amplifier (PA), adopts a differential structure with an LC tank. The VCO frequency can be tuned from 770 MHz to 970 MHz by changing the bias voltage of the varactors that are placed in parallel with the LC tank. The relationship between the VCO frequency and the tuning voltage is presented in FIG. 4. The VCO signal is amplified by a differential buffer and is converted to a single-ended signal. It is then fed to an on-chip PA for more amplification.

The PA has a cascode topology and provides a maximum power gain of 15 dB. The output of the PA is matched to 50Ω by a combination of on-chip inductors and capacitors. The PA output signal is sent to the planar loop-gap resonator via a circulator. The flat loop-gap resonator is made in-house using a 20 mil Rogers 4350B PCB. The loop has inner and outer diameters of 4 mm and 5 mm, respectively. The loaded quality factor Q of the resonator is measured to be 60. Variable capacitors are applied in parallel and series, to tune the resonance frequency and match the input impedance to 50Ω.

Figure 5:
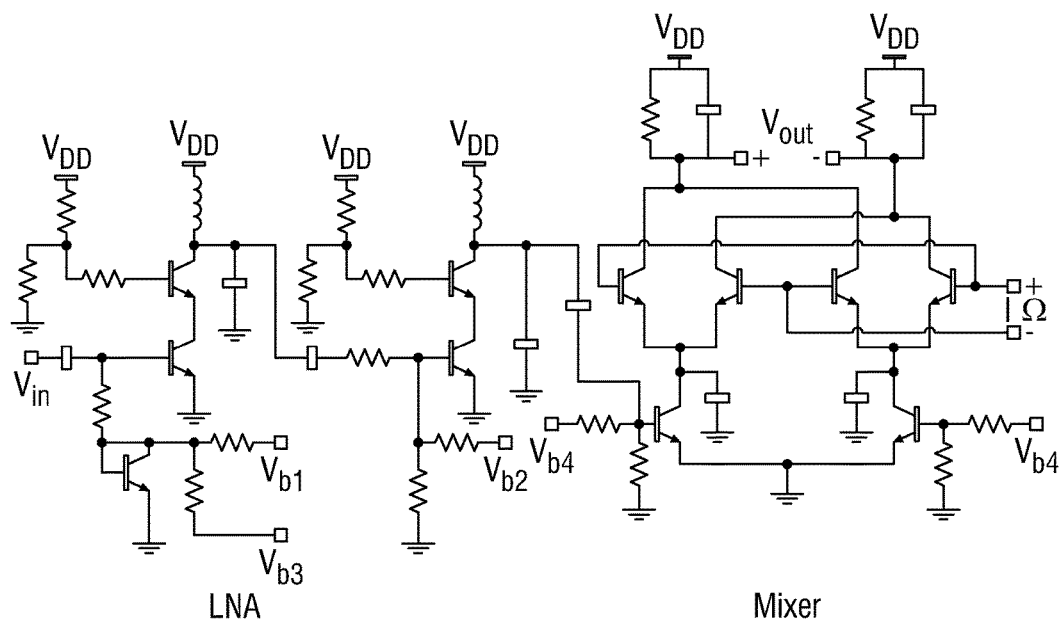
FIG. 5 is an illustration of circuit diagram for a low noise amplifier (LNA) and mixer.

On the receiving end, a direct-conversion architecture is adopted which comprises of a LNA, a mixer, and baseband amplifiers. The reflected RF signal from the sample is coupled to the input of the LNA. This signal is down-converted and its amplitude is measured at the baseband. The LNA has two stages and it is designed to have a power gain of 40 dB and a noise figure of 3.6 dB at the entire frequency range of the VCO. The designed LNA output 1 dB compression point is −15 dBm. The mixer has a Gilbert topology with a resistive load. The circuit diagrams for the LNA and the mixer are shown in FIG. 5.

Figure 6:
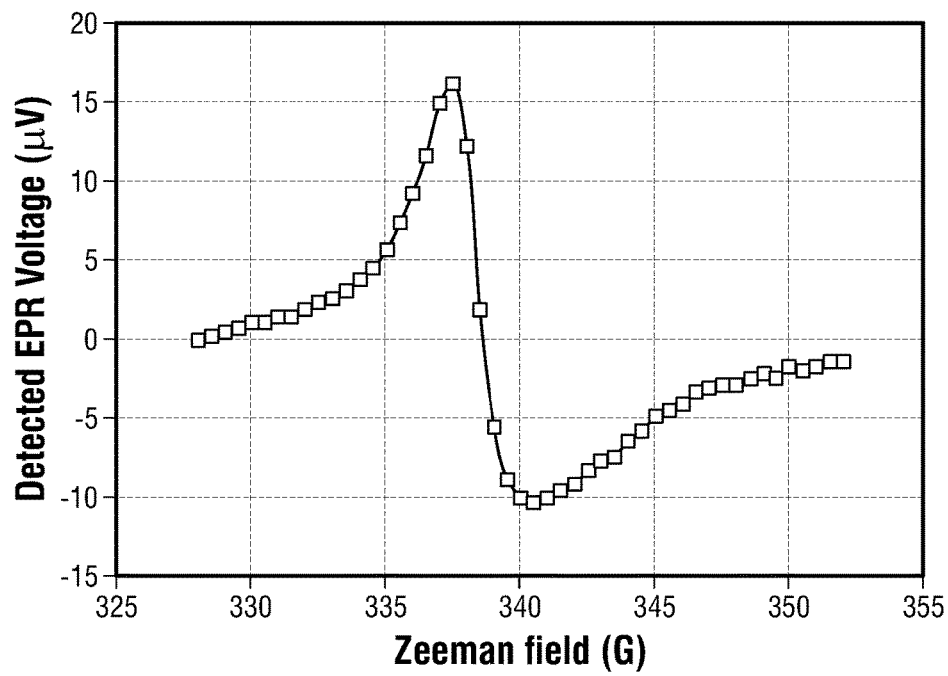
FIG. 6 is an illustration of a room-temperature CW EPR response v. DC magnetic field of a DPPH sample measured by a single-chip spectrometer.

In FIG. 6, a room-temperature CW EPR response of the DPPH sample measured by the single-chip spectrometer is reported. The Zeeman magnetic field $B_0$ is swept from 328 G to 352 G. The VCO frequency is kept constant at 950 MHz, which is the resonance frequency of the loop-gap resonator. In order not to saturate the EPR signal and not to introduce significant line broadening, the gain of the buffer and PA in the integrated transmitter is deliberately lowered and a relatively low power of −20 dBm is sent. This amount of RF power generates about 25 mG magnetic field at the center of the resonator. $B_0$ is further modulated by a 2 kHz signal with 0.27 G amplitude to reduce the Flicker (1/f) noise. The response curve in FIG. 6 is the first-derivative of the Lorentzian absorption line. There is a separation of 2.5 G in $B_0$ between the positive and negative peaks that includes the broadening effects caused by the field modulation. This matches well with the first harmonic Lorentzian line shape of DPPH powdered crystal. The difference in magnitude of the two peaks comes from the frequency dependency of the phase of the reflected signal. This effect can be minimized by employing an I-Q topology or adding a phase-shifter in the signal path.

Figure 7:
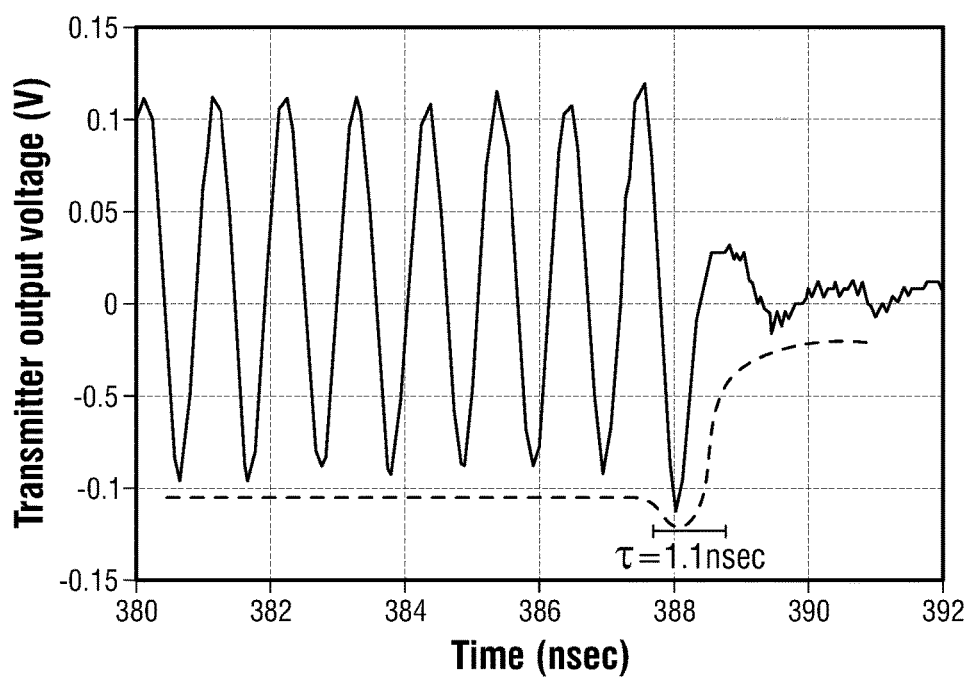
FIG. 7 is an illustration of a measured transmitter output during a switching process in a pulse mode.

In addition to the CW mode, the chip can be operated in the pulse mode. In this design, a sequence of coherent pulses is generated by an integrated programmable pulse-width modulator. The width of each pulse can be independently varied from 20 ns to 400 ns with steps of 370 ps. The PA can be turned off by pulling down the base voltage of its input transistor using an NMOS driver. In the pulse mode, the speed that a transmitter can be switched off determines the dead time of the spectrometer. Since the EPR echo is much weaker than the excitation signal, it can only be detected after switching off the transmitter. The amplitude of the EPR echo decays exponentially, and therefore, a small turn-off time is extremely important in the pulse measurements. The measured transmitter output, during the switching process, is shown in FIG. 7. The transmitter can be turned off in less than 1.2 ns.

Figure 8A:
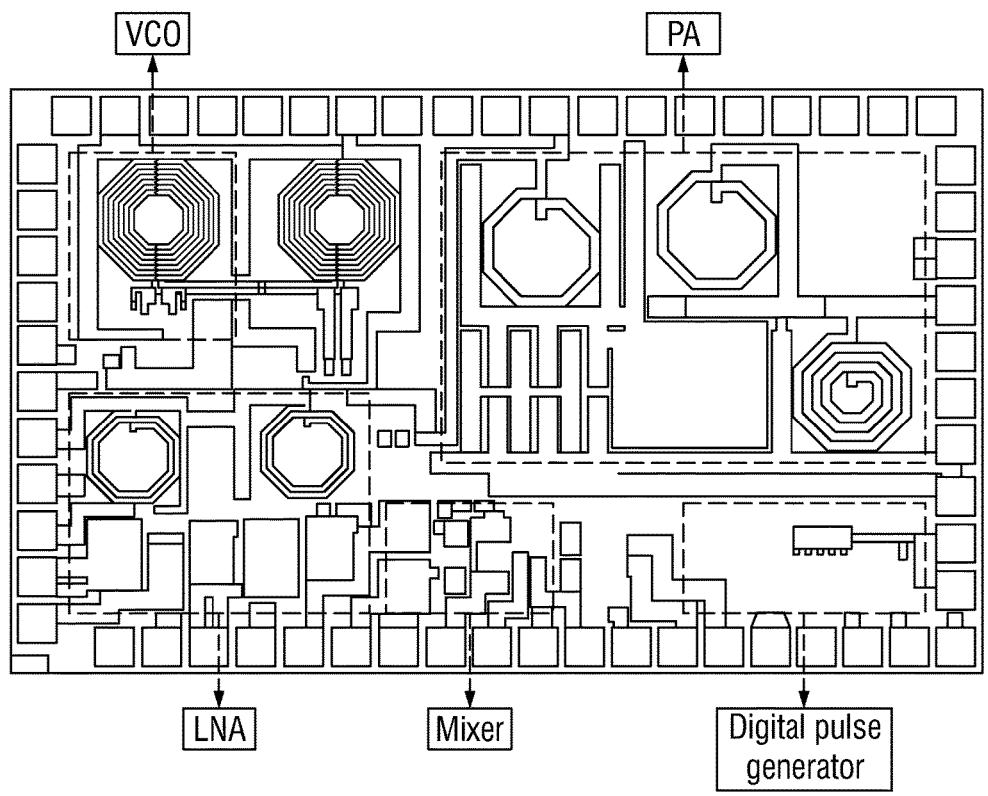
FIGS. 8A-8B are an illustrations of a micrograph of an EPR chip and image of a single-chip EPR spectrometer.
Figure 8B:
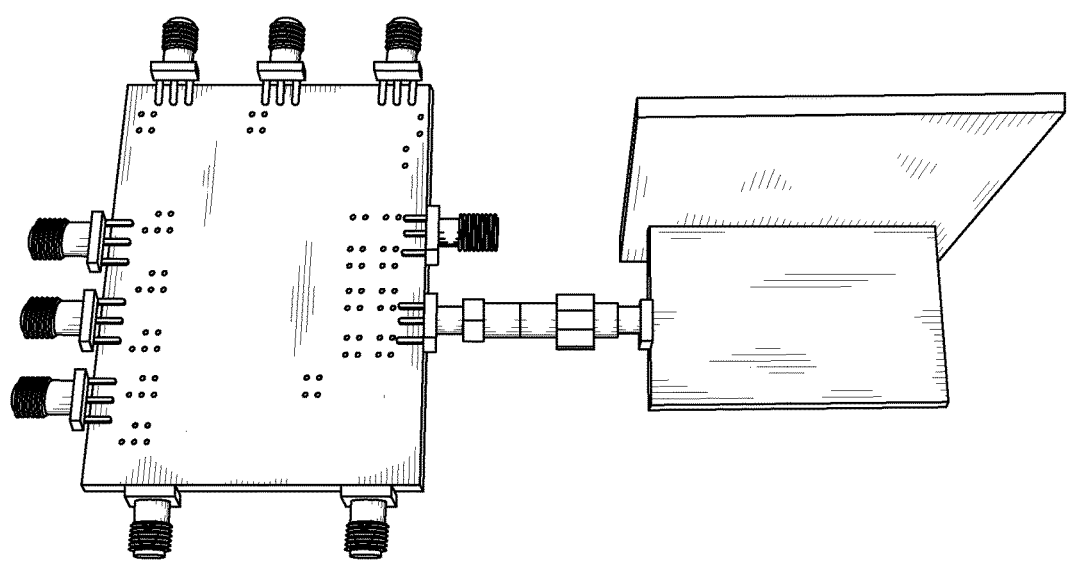

Finally, we present the chip micrograph in FIG. 8A and image of a single-chip EPR spectrometer in FIG. 8B. The chip size is 1.5 mm by 2.5 mm. It is implemented in IBM's 0.13 μm SiGe BiCMOS process technology.

Figure 9:
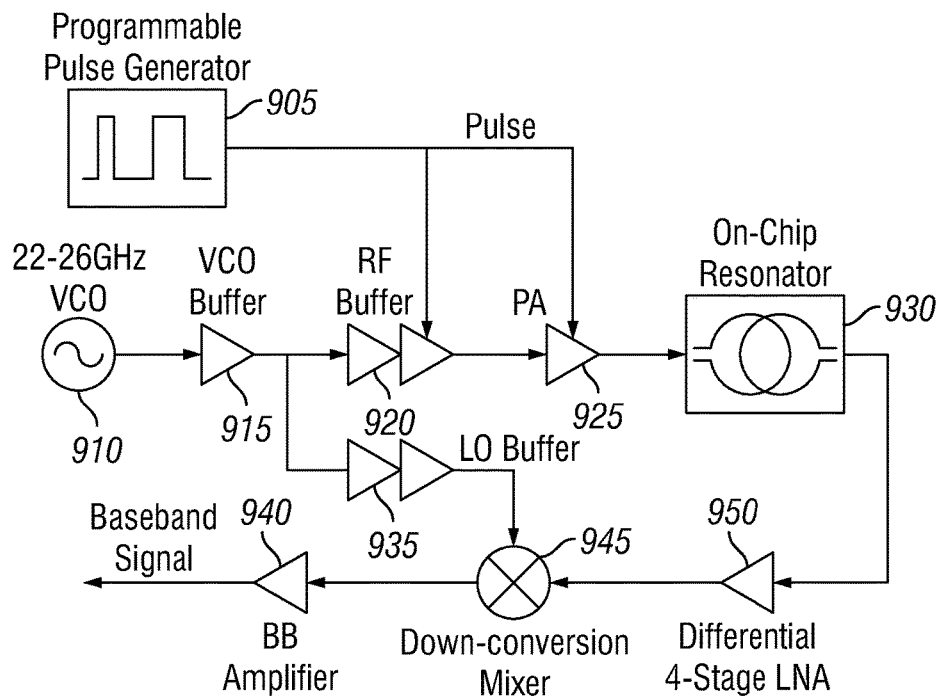
FIG. 9 is an illustrative embodiment of a block-diagram of an integrated mm-wave EPR spectrometer.

A block-diagram of an integrated EPR spectrometer is shown in FIG. 9. In a pulsed mode, pulse generator 905 may generate pulses provided to RF buffer 920 and power amplifier (PA) 925 that are provided to the resonator 930 to generate an RF magnetic field. During the first phase (excitation), the transmitter section provides an RF magnetic field on the EPR sample by controlling the output current of an on-chip resonator 930 connected to PA 925. The 30 GHz $B_1$ magnetic field generated in the resonator 930 causes flipping of electron spins. In phase two, a control pulse signal switches off the PA 925 in less than 0.5 ns. This is implemented by switching off both the PA 925 and its previous buffer stage 920, as will be explained in the following paragraphs. The sooner the transmitter turns off, the faster the time domain EPR signal can be observed. In this scheme, it is not necessary to turn off the LNA 950, as the LNA transition from saturation to linear operation is also about 0.5 ns. In the final stage (the detection phase) the four-stage differential LNA 950 amplifies the received EPR signal by 60 dB, and sends it to the mixer 945 and BB amplifier 940 for down conversion to the baseband.

The transmitter comprises a voltage controlled oscillator (VCO) 910 operating at 22 GHz to 26 GHz range, buffers 915, 920 and a power amplifier (PA) 925. The VCO topology used is a negative resistance cross-coupled transistor pair that provides the oscillator core. Differential transmission lines are used to bias the oscillator core as well as to serve as inductors to resonate with the varactor. The varactor is implemented using reverse biased diodes. Following the VCO 910 is a single-stage buffer 915 which isolates the VCO from the PA 925 and its preamplifier. This buffer ensures that the oscillation frequency remains unchanged by keeping the VCO load impedance constant during the transition from the excitation phase (PA on) to the detection phase (PA off). The VCO signal is then routed to the RF 920 and LO 935 paths, each through a two-stage buffer. In particular, the second stage of the two-stage buffer in the RF 920 path has a switch that shorts its base voltage to ground, providing a high level of isolation between the VCO output and the on-chip resonator. The PA 925 has a similar switching mechanism with an additional pull-down transistor at the base of the PA cascode transistor stage that provides further isolation. This operation allows for the VCO 910 to remain on throughout all stages, eliminating start-up time issues. The combined effect of switching the buffer and the PA provides 55 dB on/off ratio for the current on the excitation coil.

Figure 10:
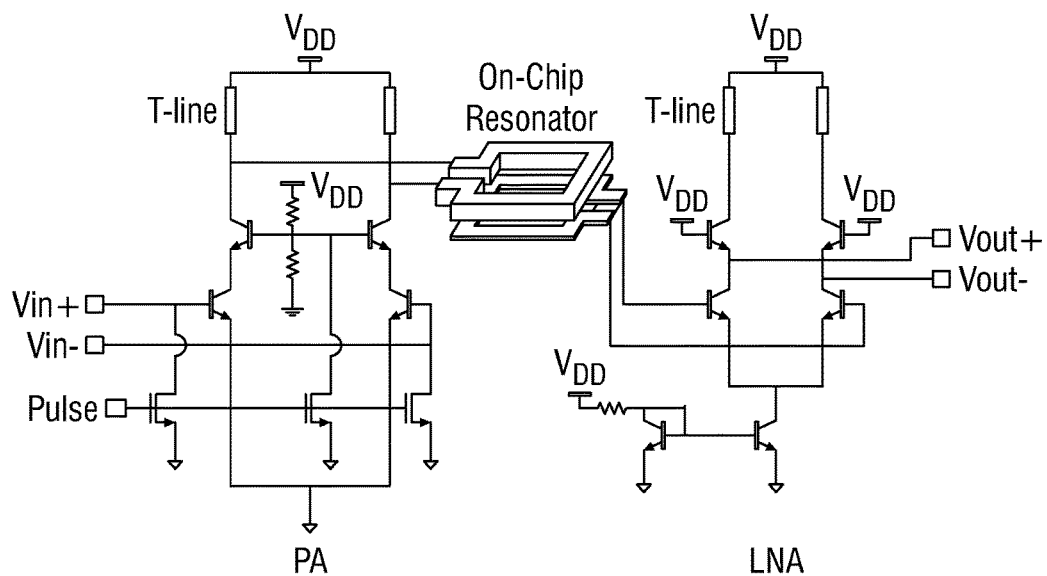
FIG. 10 is an illustrative embodiment a mm-wave spectrometer core comprises a PA, resonator and LNA.

The spectrometer core comprises the PA, resonator and the LNA is shown in FIG. 10. The PA employs a differential cascode topology which converts the input power to an RF current on the excitation coil. In order to maximize this current, the PA output matching network is optimized using on-chip transmission lines. Top metal layers with low sheet resistances (0.007/square for 7th layer and 0.037/square for 5th layer) are used for the coils in order to make high quality factor resonators. The excitation coil size is 20 μm and it produces a B1 field of 20 Gauss by a current of 16 mA. This is sufficient for generating a 90 degree flip angle of ~100 ns long.

Figure 11:
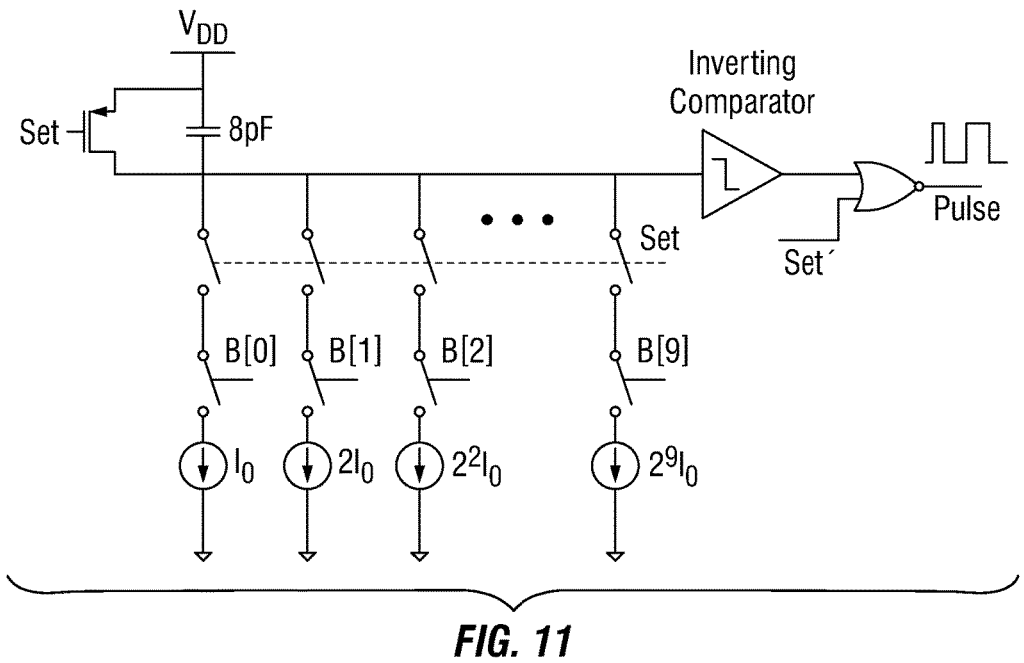
FIG. 11 is an illustrative embodiment a programmable pulse generator capable of producing digital pulses.

A programmable pulse generator capable of producing digital pulses with pulse widths ranging from 0.5 ns-500 ns is integrated, as shown in FIG. 11. The pulse width is determined by the time it takes for the capacitor to discharge from the supply voltage to a threshold voltage. The "Set" signal charges the capacitor on falling edges through the pullup PMOS transistor and discharges it through the current sources on rising edges. Ten binary scaled current sources, each representing a digital bit, control the rate at which the capacitor discharges and therefore the pulse width. This is equivalent to having pulse width resolution of 0.5 ns. The comparator and the NOR gate are used to identify the rising edge of the Set signal and the rising edge of the comparator output.

On the receiver side, a four-stage variable-gain LNA providing a gain of 60 dB is implemented to amplify the EPR signal. Each LNA uses differential cascode topology. The LNA input matching circuit is designed to maximize the LNA gain and match it to the detection coil. Following the LNA is a down-conversion mixer. The mixer uses double-balanced Gilbert cell topology. 50 resistors are used to degenerate the mixer in order to improve the linearity. The demodulated signal is finally amplified by the baseband amplifier which employs a differential amplifier matched to a differential output impedance of 100.

III. Measurement Results

Figure 12:
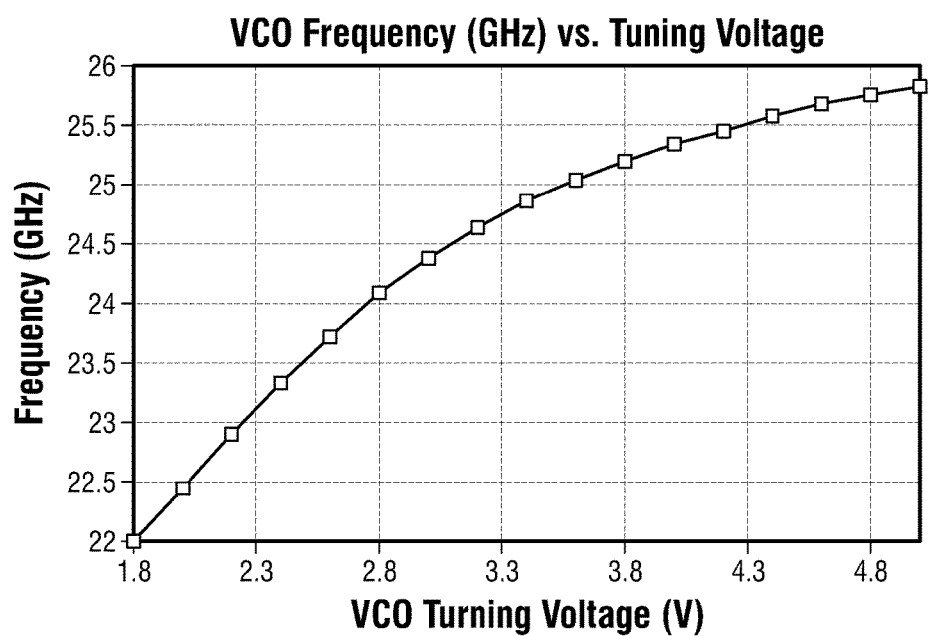
FIG. 12 shows a measured VCO frequency versus tuning voltage.
Figure 13:
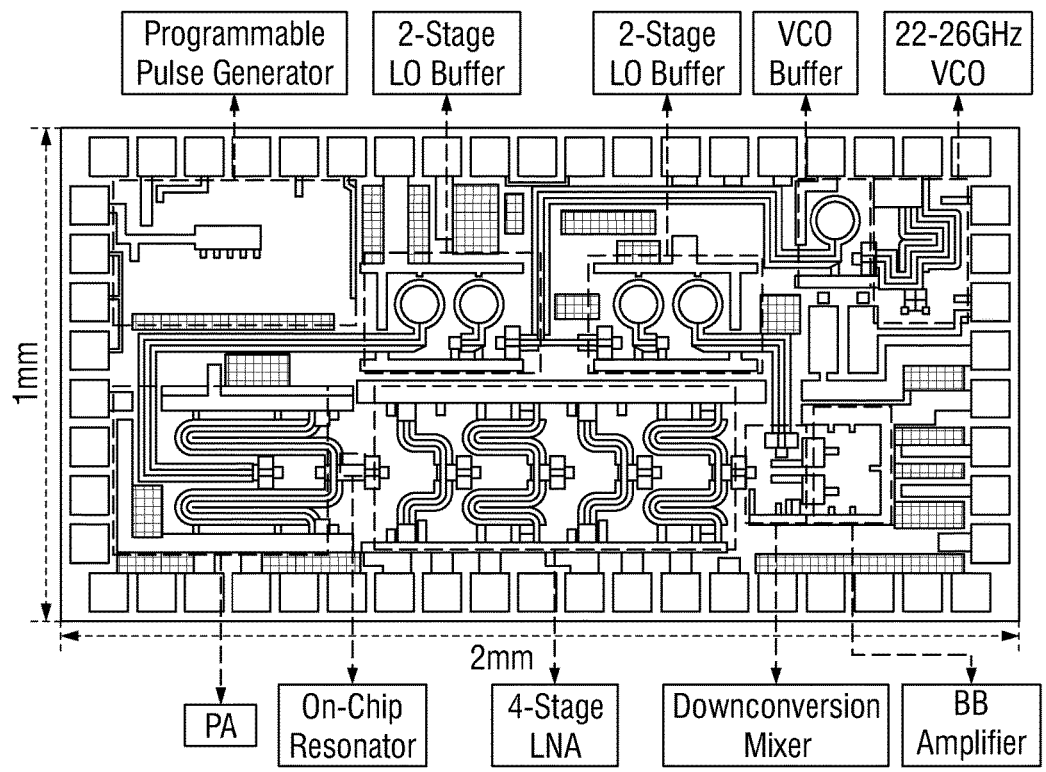
FIG. 13 is another illustration of a micrograph for a mm-wave pulse EPR spectrometer.

The chip is fabricated in IBM's 0.13 μm SiGe BiCMOS process technology. FIG. 12 shows the measured VCO frequency versus the tuning voltage. The frequency ranges from 22-26 GHz for a tuning voltage of 1.8V-5V, which corresponds to ~16% tuning range. The transmitter gain is 936 A/W, which is calculated by dividing the excitation current by the VCO output power. The receiver has a gain of 244 W/A, which is calculated by dividing the baseband output power on a 50 load by the detection current. The size of the chip is 1 mm by 2 mm. The power consumption for the whole chip is 385 mW. Table 1 shows summary of the chip performance and FIG. 13 shows the chip micrograph.

Figure 14:
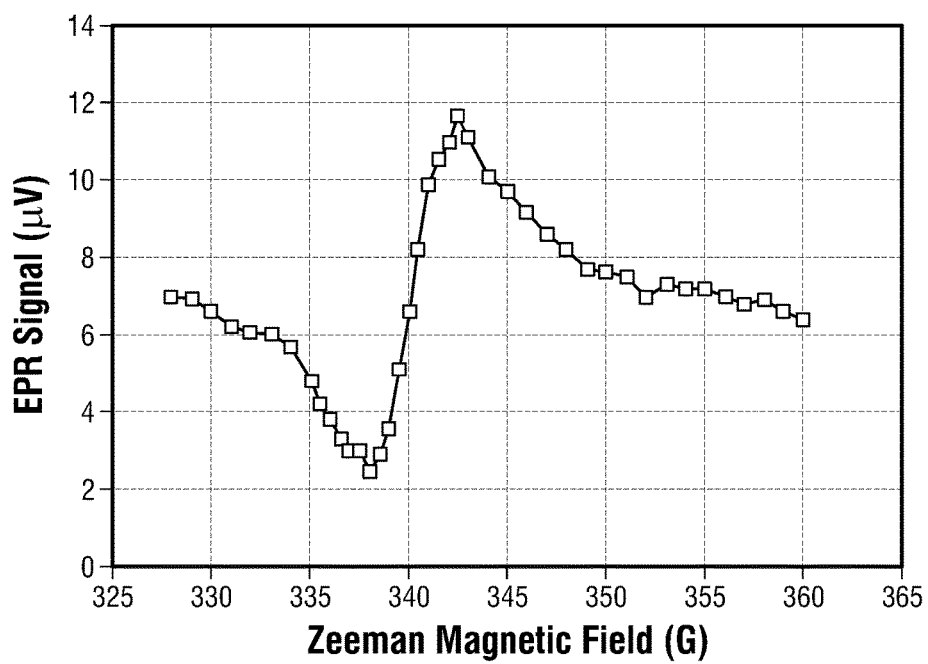
FIG. 14 shows a measured EPR spectrum of asphaltenes powder extracted from crude oil measured by the EPR chip in FIG. 8A.

In addition to the EPR measurements of DPPH powder, we have used our 1 GHz spectrometer to characterize EPR line-shape of asphaltenes. FIG. 14 shows the measured EPR spectrum of asphaltenes powder extracted from crude oil.

Figure 15A:
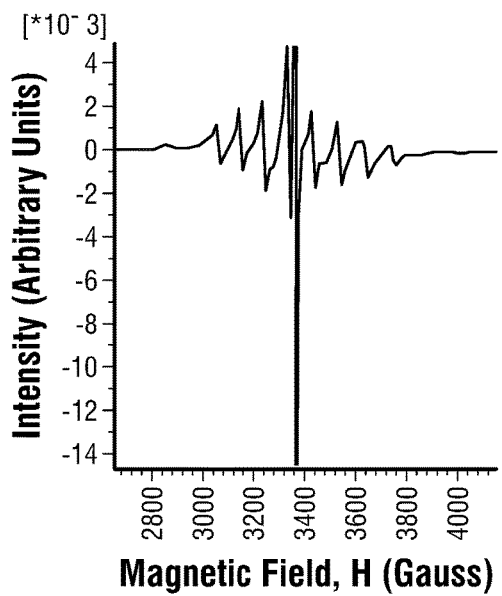
FIGS. 15A-15B show EPR spectrums of 4% Boscan asphaltene solution in o-xylene at 100° C. and 25° C., respectively.
Figure 15B:
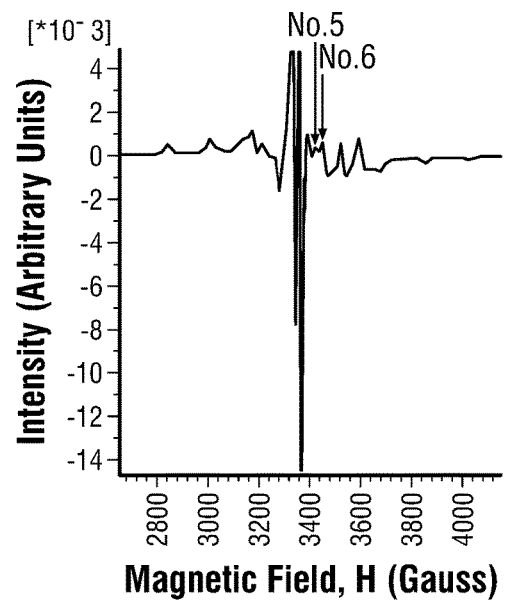

In addition to asphaltenes, the technique of EPR can be used to study behavior of asphaltenes solution in different temperatures. FIGS. 15A-15B shows the EPR vanadyl hyperfine lines as the temperature of a 4% Boscan asphaltene solution in o-xylene increased from 25° C. to 100° C.

Figure 16:
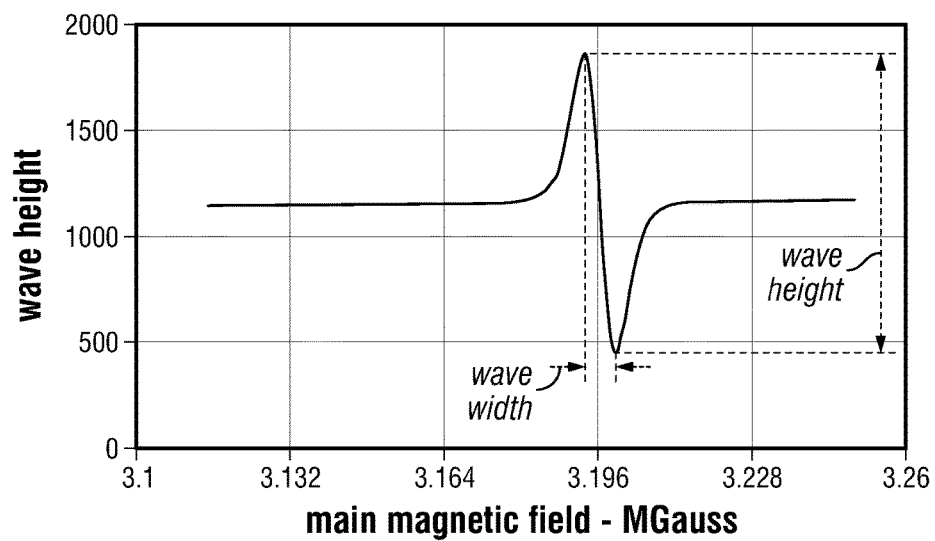
FIG. 16 shows an example of EPR response curve.

Other applications of a miniaturized EPR sensor include:
1) Asphaltene content determination (Saturate, Aromatic, Resin and Asphaltene SARA analysis, which is an analysis method that divides crude oil components according to their polarizability and polarity)
2) Core flooding
3) Capillary deposition experiments
4) High pressure/temperature study of asphaltene precipitation Experiments to study the relationship between the EPR response curve and the concentration/precipitation level of the asphaltene solution were performed as well. The focus was on two important parameters of the EPR response curve: the wave width and the wave height, as labeled in FIG. 16.

In the first measurement, two samples were prepared. One sample contains pure asphaltene powder, which can be regarded as 100% precipitated asphaltene. The other sample contains crude oil in which aspaltene is dissolved. The EPR response curve of each samples are measured for three times, and the average wave widths, as well as standard errors for each sample, are shown in Table 1 below. As the difference in wave width between these two samples is much larger than the standard error, it is clear that the wave width increases with asphaltene precipitation.

TABLE 1

| | average wave width (KG) | standard error |
|---|---|---|
| Liquid | 5.9257 | 0.1305 |
| Powder | 6.6302 | 0.2121 |

In the second measurement, four different asphaltene solutions were prepared. Each sample has the same asphaltene concentration, but different amount of heptane: 0%, 50%, 67%, and 75%. The EPR response curve of each samples are measured for ten times, and the averaged measurement results are plotted in FIG. 17. It is observed that the EPR response of samples with a higher amount of heptane has a larger wave width. As a higher amount of heptane results in more precipitated asphaltene, the results of this measurement is consistent with the results of measurement 1, that is the wave width increases with asphaltene precipitation.

Figure 18:
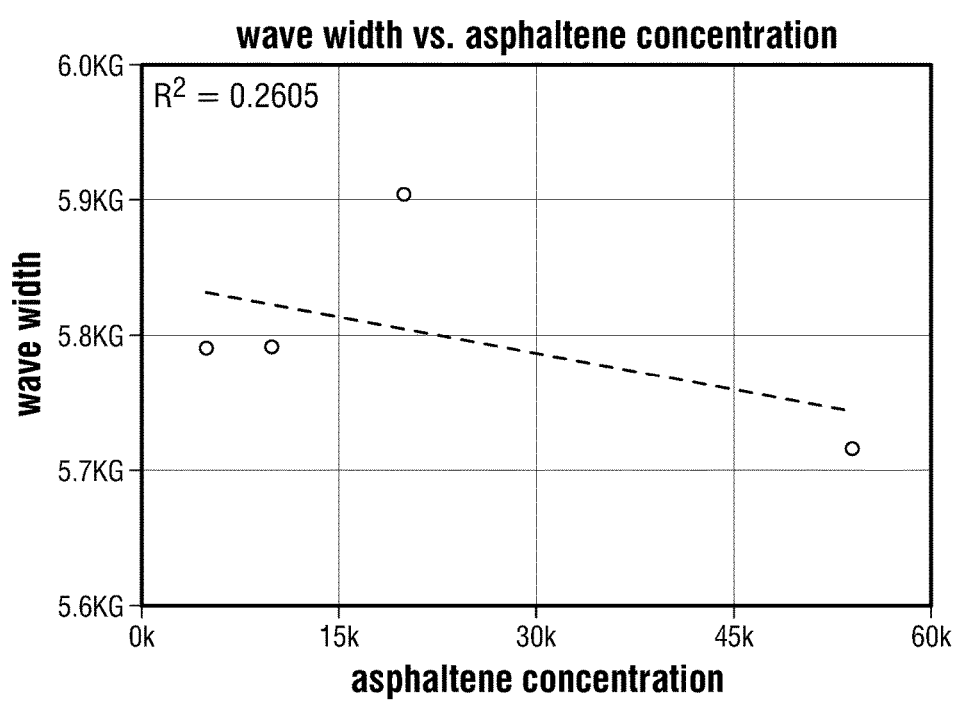
FIG. 18 shows wave width v. asphaltene concentration.
Figure 19:
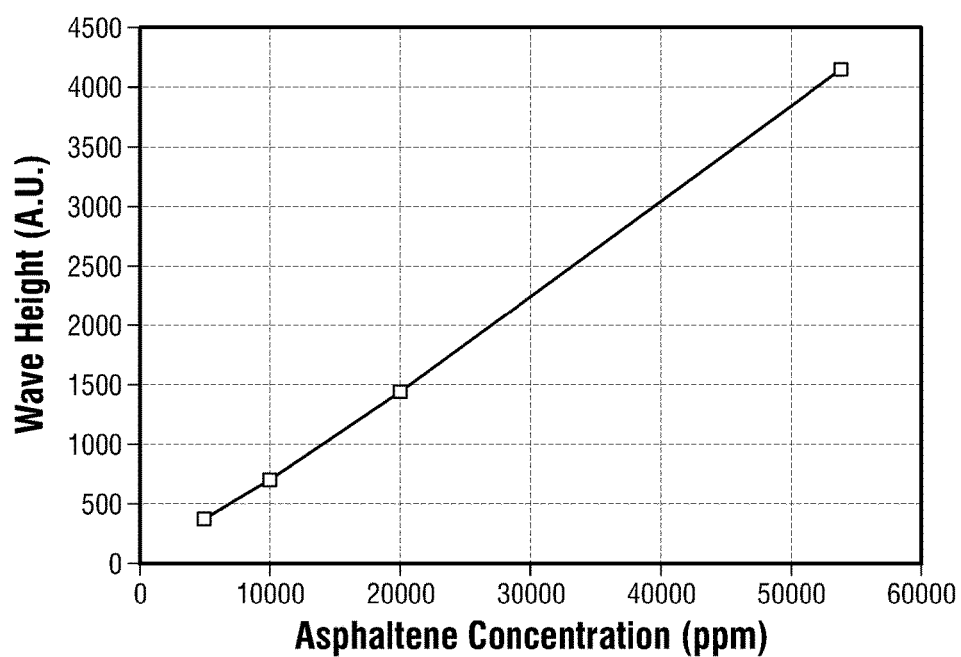
FIG. 19 shows the wave height v. asphaltene concentrations.

In the third measurement, four samples with no heptane (and hence no precipitated asphaltene), but different asphaltene concentration are prepared to study the effects of asphaltene concentration on the EPR response curve. The asphaltene concentration varies from 5000 ppm, 10000 ppm, 20000 ppm, to 54000 ppm. The EPR response curve of each samples are measured for ten times, and the averaged measurement results are plotted in FIG. 18 and FIG. 19. As shown in FIG. 18, the asphaltene concentration does not have a strong impact on the EPR wave width, indicated by a small R2 value. However, it is observed that the EPR wave height is proportional to the EPR concentration, as shown in FIG. 19.

It is noted that the above EPR response curves were obtained by taking multiple measurements and averaging the values to ensure accuracy and to reduce errors.

Figure 17:
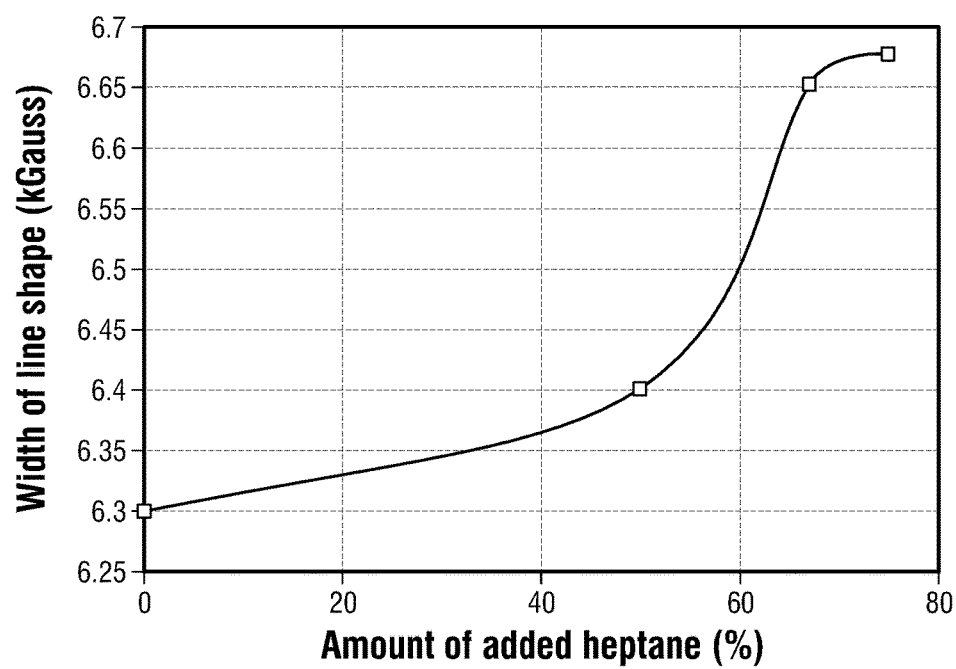
FIG. 17 shows a wave width v. heptane concentration curve.

It is apparent from the result that the EPR line shapes can be used to determine the concentration and precipitation of the asphaltene in the flow. FIG. 19 shows the height of the EPR line shape versus asphaltene solution (dissolved in toluene) with different concentration. The height is observed to be proportional to the asphaltene concentration. FIG. 17 shows the width of the EPR line shape versus asphaltene solution (dissolved in toluene) with different amount of heptane. It is known that a higher amount of heptane results in more precipitated asphaltene. As presented in FIG. 17, it is clear that the width of the EPR line shape increases with asphaltene precipitation. Thus, the experimental data reveals that for asphaltene solution (dissolved in toluene), the wave width increases with asphaltene precipitation, while the wave height is proportional to the asphaltene concentration.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. An apparatus for electron paramagnetic resonance (EPR) monitoring of a pipeline or well, the apparatus comprising:
    a window provided in a tubular of a pipeline or a downhole tool; and
    an EPR sensor for monitoring fluid flowing through a predominantly straight section of the pipeline or a well, wherein the EPR sensor comprises
        a transceiver that generates a signal,
        a loop-gap resonator coupled to the transceiver, wherein the resonator generates a RF magnetic field from the signal received from the transceiver, and the transceiver and resonator are positioned adjacent to the window to allow the RF magnetic field to reach the fluid, and
        a magnetic field generator positioned near the resonator, wherein the magnetic field generator provides a DC magnetic field that is approximately normal to the RF magnetic field, and a sample being measured intersects a center volume of the DC magnetic field that is generated.

2. The apparatus of claim 1, wherein a size of the EPR sensor is equal to or less than 100 cm$^3$.

3. The apparatus of claim 1, wherein a weight of the EPR sensor is 10 kg or less.

4. The apparatus of claim 1, wherein the EPR sensor is capable of detecting asphaltenes concentrations of 10000 ppm or less when positioned a distance of 3 inches or less from the fluid.

5. The apparatus of claim 1, wherein the signal produced by the EPR sensor is a continuous wave or pulsed signal.

6. The apparatus of claim 1, wherein the transceiver monitors a change in a reflected power of the RF magnetic field to determine an amount of RF power absorbed the fluid.

7. The apparatus of claim 6, wherein the apparatus monitors a wave width, wave height, zero-crossing point, or a combination thereof of the RF power absorbed to determine paramagnetic properties of the fluid.

8. The apparatus of claim 1, wherein the transceiver monitors a precession of a transverse component of a magnetization vector around the DC magnetic field to detect a time-domain signal.

9. The apparatus of claim 8, wherein a longitudinal relaxation due to spin-lattice interaction (T1) and/or transverse relaxation due to spin-spin interaction (T2) may be measured.

10. The apparatus of claim 1 further comprising an active cancelation block, wherein the active cancelation block reduces a leakage signal coupled to an input of a receiver from a transmitter.

11. The apparatus of claim 1, wherein the transceiver is a single-chip transceiver.

12. The apparatus of claim 1, wherein the EPR sensor operates at 100 MHz or higher.

13. A method for electron paramagnetic resonance (EPR) monitoring of a pipeline or well, the method comprising:
    positioning an EPR sensor near a window in a predominantly straight section of a tubular of a pipeline or a downhole tool for monitoring fluid flowing through the pipeline or a well, wherein the EPR sensor comprises
        a transceiver that is capable of generating a signal,
        a loop-gap resonator coupled to the transceiver,
        wherein the resonator generates a RF magnetic field from the signal received from the transceiver, and
        a magnetic field generator;
    positioning the magnetic field generator near the resonator, wherein the magnetic field generator supplies a DC magnetic field; and
    generating the signal with the transceiver so that the resonator generates a RF magnetic field corresponding to the signal that is approximately normal to the DC magnetic field, and a sample being measured intersects a center volume of the DC magnetic field that is generated.

14. The method of claim 13, wherein the monitoring step further comprises the steps of:
- monitoring an amount of RF power absorbed by fluid flowing through the pipeline or well as a function of the DC magnetic field;
- plotting the amount of RF power absorbed versus the DC magnetic field in real-time to provide a RF power absorption plot; and
- monitoring a line shape of the RF power absorption plot.

15. The method of claim 13, wherein a wave width, wave height, zero-crossing point, or a combination thereof of the RF power absorption plot is monitored to determine paramagnetic properties of the fluid.

16. The method of claim 15, wherein the wave height determines a concentration of asphaltenes and the wave width determines an amount of asphaltenes that is aggregated.

17. The method of claim 13, wherein the monitoring step further comprises the steps of:
- monitoring an amount of RF power absorbed by fluid flowing through the pipeline or well as a function of a frequency of the signal;
- plotting the amount of RF power absorbed versus the frequency of the signal in real-time to provide a RF power absorption plot; and
- monitoring a line shape of the RF power absorption plot.

18. The method of claim 13, wherein the monitoring step further comprises the steps of:
- monitoring a time-domain signal generated by the fluid; and
- monitoring a longitudinal relaxation due to spin-lattice interaction (T1) and/or transverse relaxation due to spin-spin interaction (T2).

19. The method of claim 13, wherein a size of the EPR sensor is equal to or less than 100 $cm^3$.

20. The method of claim 13, wherein a weight of the EPR sensor is 10 kg or less.

21. The method of claim 13, wherein the EPR sensor is capable of detecting asphaltenes concentrations of 10000 ppm or less when positioned a distance of 3 inches or less from the fluid.

22. The method of claim 13, wherein the EPR sensor operates at 100 MHz or higher.

* * * * *